United States Patent [19]
Quackenbush et al.

[11] Patent Number: 6,102,881
[45] Date of Patent: Aug. 15, 2000

[54] HINGED DROP FOOT BRACE

[75] Inventors: Todd R. Quackenbush, 18016 Stone Ave. N., Seattle, Wash. 98133; Timothy C. Vittetoe, Redmond, Wash.

[73] Assignee: Todd R. Quackenbush, Seattle, Wash.

[21] Appl. No.: 09/298,815

[22] Filed: Apr. 23, 1999

[51] Int. Cl.[7] .................. A61F 5/00; A61F 5/14; A43B 7/14; A43B 7/16

[52] U.S. Cl. .................. 602/28; 602/16; 602/27; 36/140; 36/88; 36/92

[58] Field of Search ................. 602/5, 16, 23, 602/27, 28, 29, 65; 128/877, 878, 881, 882; 36/140, 158, 169, 171, 173, 182, 88, 89, 90, 91, 92, 109, 118.2, 118.3, 118.4

[56] References Cited

U.S. PATENT DOCUMENTS

| | | |
|---|---|---|
| D. 391,640 | 3/1998 | Oviedo, Jr. . |
| 1,332,047 | 2/1920 | Lasher . |
| 1,356,327 | 10/1920 | Winiarski . |
| 1,402,282 | 1/1922 | Chevrier . |
| 1,598,504 | 8/1926 | Pierce et al. . |
| 2,439,100 | 4/1948 | Richards . |
| 2,440,894 | 5/1948 | Caesar . |
| 2,444,839 | 7/1948 | Markkula . |
| 2,525,237 | 10/1950 | Park . |
| 2,567,195 | 9/1951 | Ellery . |
| 2,573,698 | 11/1951 | Ellery . |
| 2,663,294 | 12/1953 | Harrison . |
| 2,847,991 | 8/1958 | Andrews . |
| 2,871,851 | 2/1959 | Swanson . |
| 2,874,690 | 2/1959 | Cowgill . |
| 3,527,209 | 9/1970 | Baker . |
| 3,589,359 | 6/1971 | Hill . |
| 3,765,409 | 10/1973 | Merkle . |
| 3,859,991 | 1/1975 | Theodores . |
| 3,916,886 | 11/1975 | Rogers . |
| 3,986,501 | 10/1976 | Schad . |
| 4,329,982 | 5/1982 | Heaney . |
| 4,566,447 | 1/1986 | Deis . |
| 4,651,723 | 3/1987 | Satoh . |
| 4,817,589 | 4/1989 | Wertz . |
| 5,259,834 | 11/1993 | Wittmeyer . |
| 5,382,224 | 1/1995 | Spangler . |

*Primary Examiner*—Kim M. Lee
*Attorney, Agent, or Firm*—Keith A. Cushing

[57] ABSTRACT

A drop foot brace includes an upper support bearing against the rear lower leg and a lower support bearing against the rear heel. A springed hinge couples the upper and lower supports and biases the upper and lower supports against the rear of the user's leg and rear of the user's heel, respectively. A shoe maintains the springed hinge against the rear of the user's leg in the vicinity of the user's ankle whereby the user experiences a lifting force in opposition to drop foot. The brace needs no coupling to the body and includes sufficient flexibility to facilitate comfort when not in use while still providing aid against foot drop. One form of the foot brace includes the heel or foot support integrally formed within a shoe and including a slot formation receiving the remaining portions of the brace whereby the brace may be easily removed from the shoe when not needed.

19 Claims, 8 Drawing Sheets

HINGED DROP FOOT BRACE

BACKGROUND OF THE INVENTION

The present invention relates generally to prosthetic devices and particularly to a prosthetic device for persons suffering a condition known as "drop foot."

Individuals afflicted with drop foot, also sometimes referred to as "foot drop", do not have full control over muscles that raise and lower the foot. Most troublesome is an inability to raise the foot when walking. The condition compromises the nerves normally conducting electrical impulses from the brain resulting in signal blockage either entirely or occasionally without warning. The toe of the foot often cannot be positioned to clear the ground as the person walks along. Consequently, the person's toe or inside edge of the foot drags on the ground while walking. The afflicted individual thereby experiences, sometimes spontaneously, an inability to walk, an inability to walk in normal fashion, or a risk of potential injury by stumbling and falling while attempting to walk.

A variety of devices have been proposed to aid the person in overcoming this condition, i.e., apparatus secured to the leg and ankle and to the shoe to prevent tripping or stumbling or dragging the foot while walking. Unfortunately, none of these devices are popular for their bulky, heavy, cumbersome, and uncomfortable aspects. Most such devices are difficult to mount and dismount and present significant inconvenience to persons wishing to temporarily remove the device when not needed, i.e., when not walking or when relaxing in particular postures including sitting positions where one desires more complete flexibility of the ankle to achieve a comfortable position. Finally, all of these devices lack significant concealment features and manifest themselves to the user and to others as bulky contraptions when in use.

U.S. Pat. No. 3,916,886 issued Nov. 4, 1975 to Rogers, et al and entitled "Preformed Self-Conforming Drop Foot Brace" shows a rigid structure running from the calf muscle down the back of the leg, around the heel, and under the foot. This structure restricts the foot to a 90 degree maximum extension. In other words, the person cannot point their toe out to form a greater than 90 degree angle between the leg and foot. In this restricted range of movement, the toe cannot drop and drag upon the ground and the person avoids potential embarrassment or injury when walking. The drop foot brace by Rogers, et al thereby solves the problem of drop foot when walking. Unfortunately, this device is severely uncomfortable and restrictive especially when not walking. It is only useful when swinging the foot forward in walking and interferes with all three aspects of walking. It is like walking while wearing ski boots. It is not suitable for sitting or relaxing in a sitting posture such as with a bent ankle or relaxed foot extending outward in a other than 90 degree angle.

U.S. Pat. No. 4,651,723 issued Mar. 24, 1987 to Cowalk and entitled "Drop Foot Splint" includes a ringed leather brace encircling completely the user's ankle and including a forward and downward extension from the front of the brace down into the top of the shoe. This device is extremely uncomfortable because of the need to securely attach the brace around the leg and establish a rigid coupling between the brace and the person's leg to adequately lift the foot through the extension engaging the shoe.

U.S. Pat. No. 1,598,504 issued Aug. 31, 1926 to Pierce, et al and entitled "Ankle Brace" shows a brace attaching around the lower portion of the user's leg with a structure extending downward along the back of the leg and including a hinged coupling to a structure attached to the user's shoe, i.e., the rear of the shoe heel. The contemplated use of this brace, however, is to aid in skating and not in lifting the foot, i.e., there is no need or desire to include any active mechanism to participate in foot movement. Rather, the device is used as a fortification against lateral bending of the ankle and potential injury during a sports activity.

U.S. Pat. No. 2,874,690 issued Feb. 24, 1959 to Cowgil and entitled "Orthopedic Foot Drop Brace" shows a structure engaging the heel of the shoe and extending upward to engage the rear of the leg just above the shoe.

It would be desirable, therefore, to provide a drop foot brace establishing aid against drop foot, but also allowing for comfort and flexibility as desired when sitting or relaxing, for more convenient use in attachment and removal and for concealment when in use.

SUMMARY OF THE INVENTION

Under the present invention, forces are applied to the rear of the leg and foot in a closing fashion to lift the foot and thereby do not require any rigid attachment to the leg. An upper support bears against the rear of the leg and a lower support bears against the rear of the heel. A springed hinge couples the upper and lower supports. By maintaining the springed hinge against the rear of the ankle, the closing forces produced by the brace result in a lifting force against foot drop.

The subject matter of the present invention is particularly pointed out and distinctly claimed in the concluding portion of this specification. However, both the organization and method of operation of the invention, together with further advantages and objects thereof, may best be understood by reference to the following description taken with the accompanying drawings wherein like reference characters refer to like elements.

BRIEF DESCRIPTION OF THE DRAWINGS

For a better understanding of the invention, and to show how the same may be carried into effect, reference will now be made, by way of example, to the accompanying drawings in which.

DETAILED DESCRIPTION OF THE PREFERRED EMBODIMENTS

A brace according to the present invention adequately supports the foot to enable substantially normal walking while providing freedom of movement while either walking or in a variety of sitting or relaxing positions. One form of the present invention easily detaches and thereby allows the user to release all restrictions imposed upon foot and ankle movement when desired, e.g., when sitting or relaxing. A brace under the present invention can be light-weight and sleek thereby offering a significant concealment aspect for the persons suffering a drop foot condition.

Figure 1:
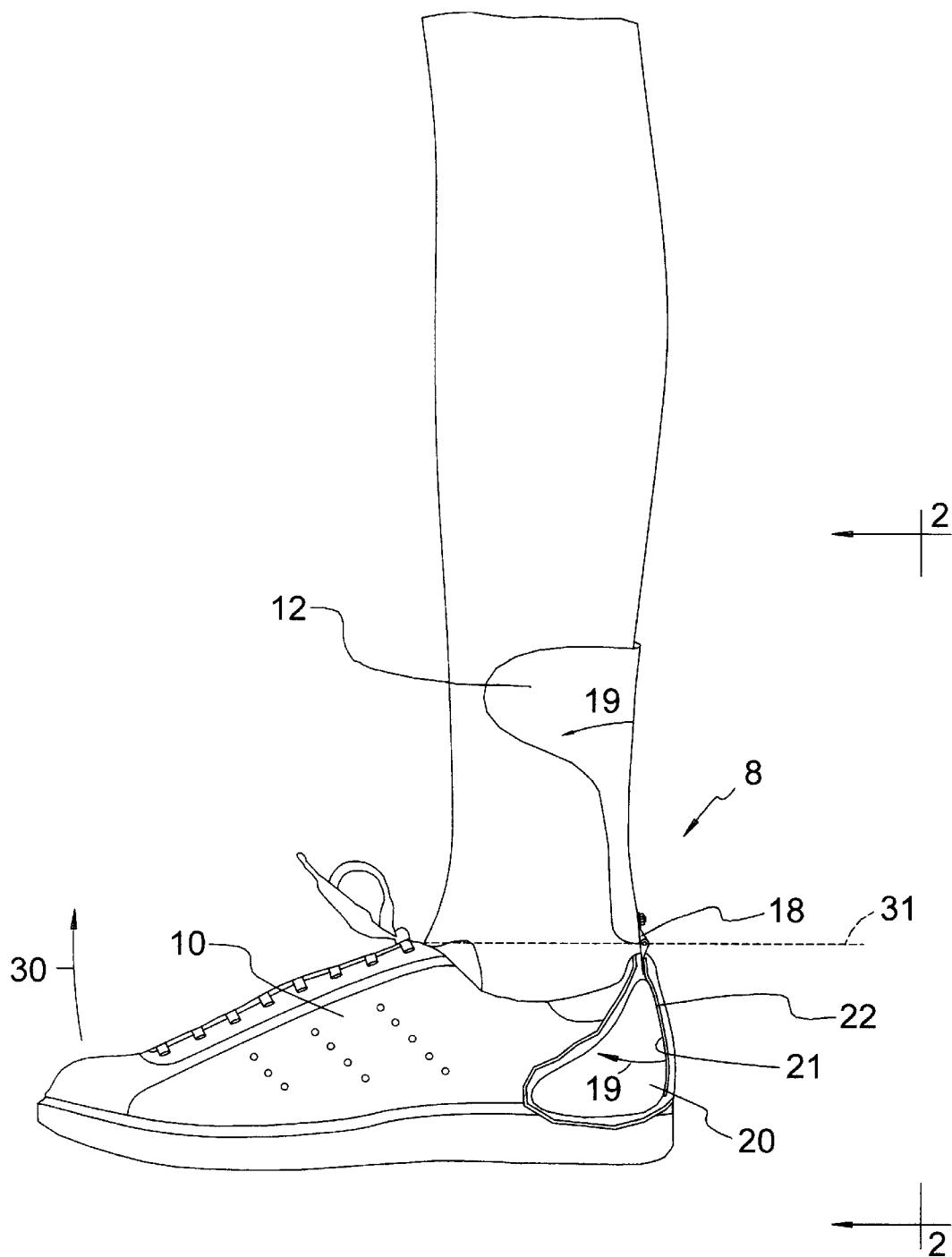
FIG. 1 is a side elevational view of a brace according to a first form of the present invention with portions of a shoe cut-away to reveal portions of the brace.
Figure 2:
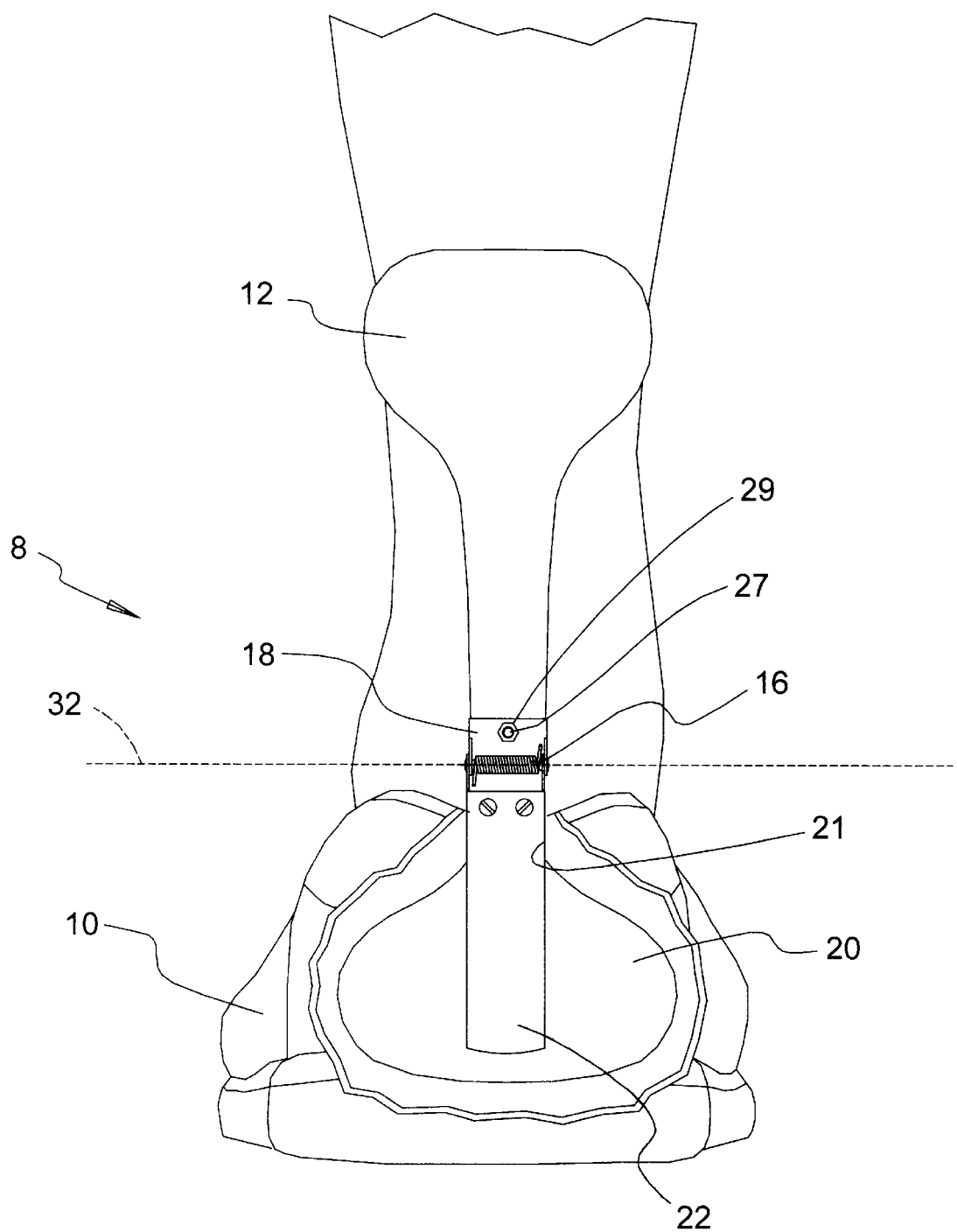
FIG. 2 is a rear elevational view as taken along lines 2—2 of FIG. 1 with portions of a shoe cut-away to reveal a formed heel support and formed extension.

FIGS. 1 and 2 show side and rear views, respectively, of a drop foot brace 8 according to a first form of the present invention. Brace 8 works in conjunction with a modified shoe 10 to aid persons suffering from drop foot, i.e., sometimes unpredictable loss of lifting control often resulting in stumbling or falling hazards for the person. A brace under the present invention may be integrally coupled to a modified shoe 10 or may include a separate structure, e.g., heel or foot cup, adapted for placement in a conventional shoe as described more fully hereafter. In this first form of the present invention, shoe 10 includes integral therewith a cupped heel support structure 20 with a slot formation 21 receiving the remaining upper portion, i.e., an extension 22, of brace 8.

Brace 8 includes a formed lower leg support 12 bearing against the back side of the user's lower leg, e.g., below or near the calf muscle. Heel support 20, integral to shoe 10, receives in its slot formation 21 the formed extension 22. A springed hinge 18 couples formed lower leg support 12 and extension 22 as coupled heel support 20. Springed hinge 18 provides "closing" forces 19 to support the user's foot against drop foot and potential embarrassment or injury resulting therefrom. More particularly, springed hinge 18 "closes" brace 8 by urging leg support 12 forward against the user's leg and heel support 20 forward against the rear of the user's heel. The net effect of closing forces 19 produced by springed hinge 18 is to gently support the foot against toe extension. As a result, the user experiences a lifting force as indicated at reference numeral 30 of sufficient magnitude to prevent drop foot and thereby prevent potential stumbling or injury. As may be appreciated, the magnitude of forces 19 produced by springed hinge 18 will dictate the magnitude of lifting force 30 experienced by the user. For those persons requiring greater assistance in preventing drop foot, a larger magnitude force need be produced at springed hinge 18.

Figure 3:
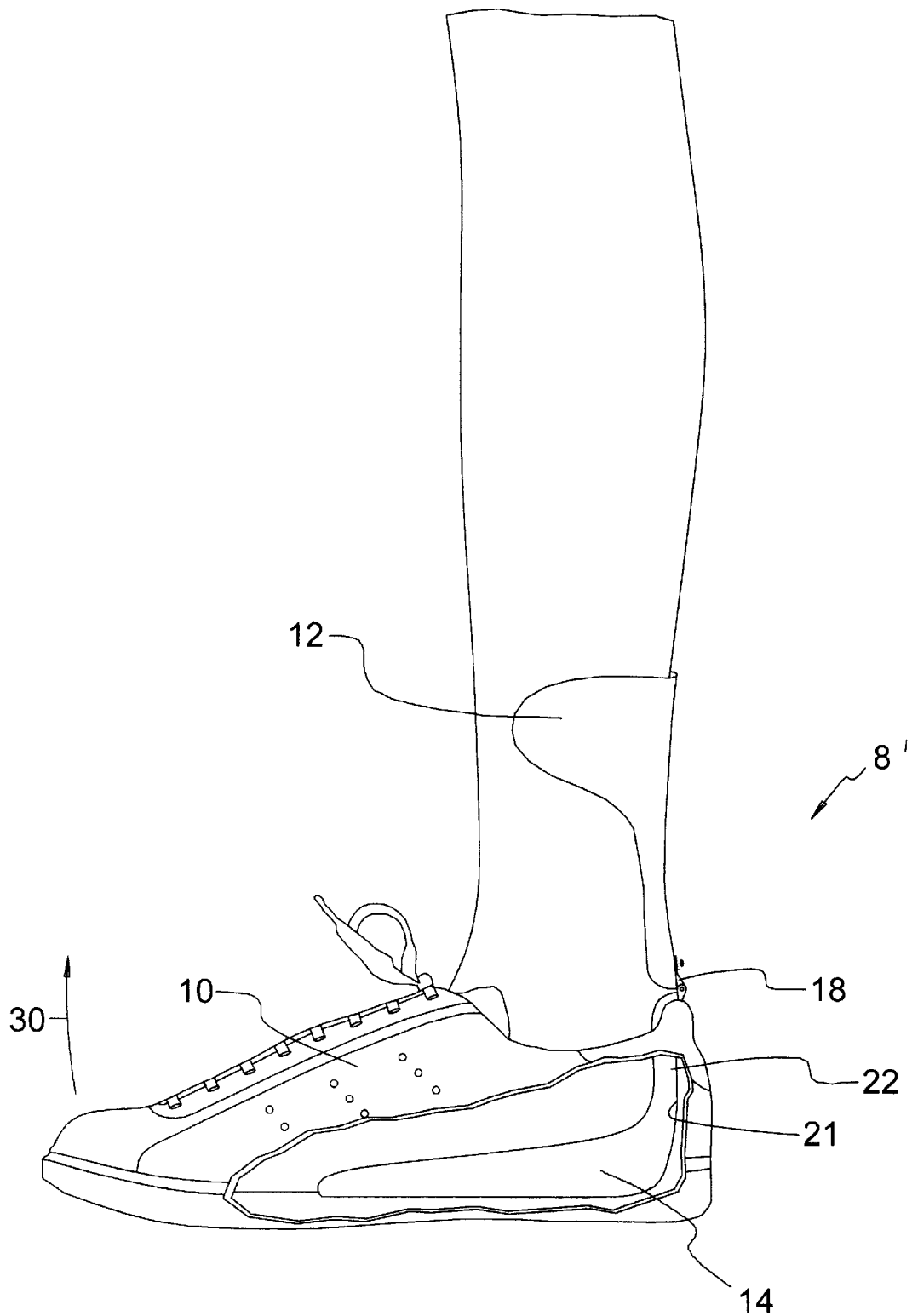
FIG. 3 is a side elevational view of a second form of the present invention including a foot support in place of a heel support.

FIG. 3 illustrates a second form of the invention, i.e., brace 8', including a support structure 14 extending further under the user's foot, i.e., the formed foot support 14. Foot support 14 is integrally formed within shoe 10 as is heel support 20. Formed foot support 14 thereby replaces the heel support 20 illustrated in FIGS. 1–2 and provides an extended degree of support beyond heel support by lifting from under the foot as opposed to lifting at the heel. In either case, a good coupling between brace 8 or brace 8' and shoe 10 better aids in lifting the user's foot upward to avoid the hazards of drop foot. Brace 8' also includes a slot 21, in foot support 14, for receiving the extension 22 and otherwise operates in substantially the same fashion as brace 8 of FIGS. 1 and 2. It will be understood, therefore, that subsequent discussion of brace 8' is in most cases equally applicable to brace 8.

While, as discussed and illustrated more fully hereafter, heel support 20 or foot support 14 need not be integrally formed into a modified shoe 10. Use of an unmodified or conventional shoe 10 and an insertable heel support 20 or formed foot support 14, i.e., independent of the shoe, provides certain advantages with respect to general purpose or generic use of a brace under the present invention for multiple shoes. It is more difficult, however, to provide the optimum functionality, i.e., optimum hinge 18 placement, when making a brace generally usable for a variety of shoe types.

By integrating the heel support 20 or formed foot support 14 into a modified shoe 10 one precisely positions brace 8 or 8' with respect to the user's anatomy to optimize its performance. More particularly, it feels like wearing only a shoe rather than a prosthetic brace because hinge 18 is strategically located to correspond with the bend of the user's ankle so as to interfere as little as possible with comfort and use of the foot during walking or sitting postures. In other words, brace 8 or 8' bends where the user's ankle bends and therefore interferes little with ankle activity. Thus, integrating the heel support 20 or formed foot support 14 into a modified shoe 10 provides better positioning of hinge 18 and, therefore, better overall operation of brace 8.

Figure 4:
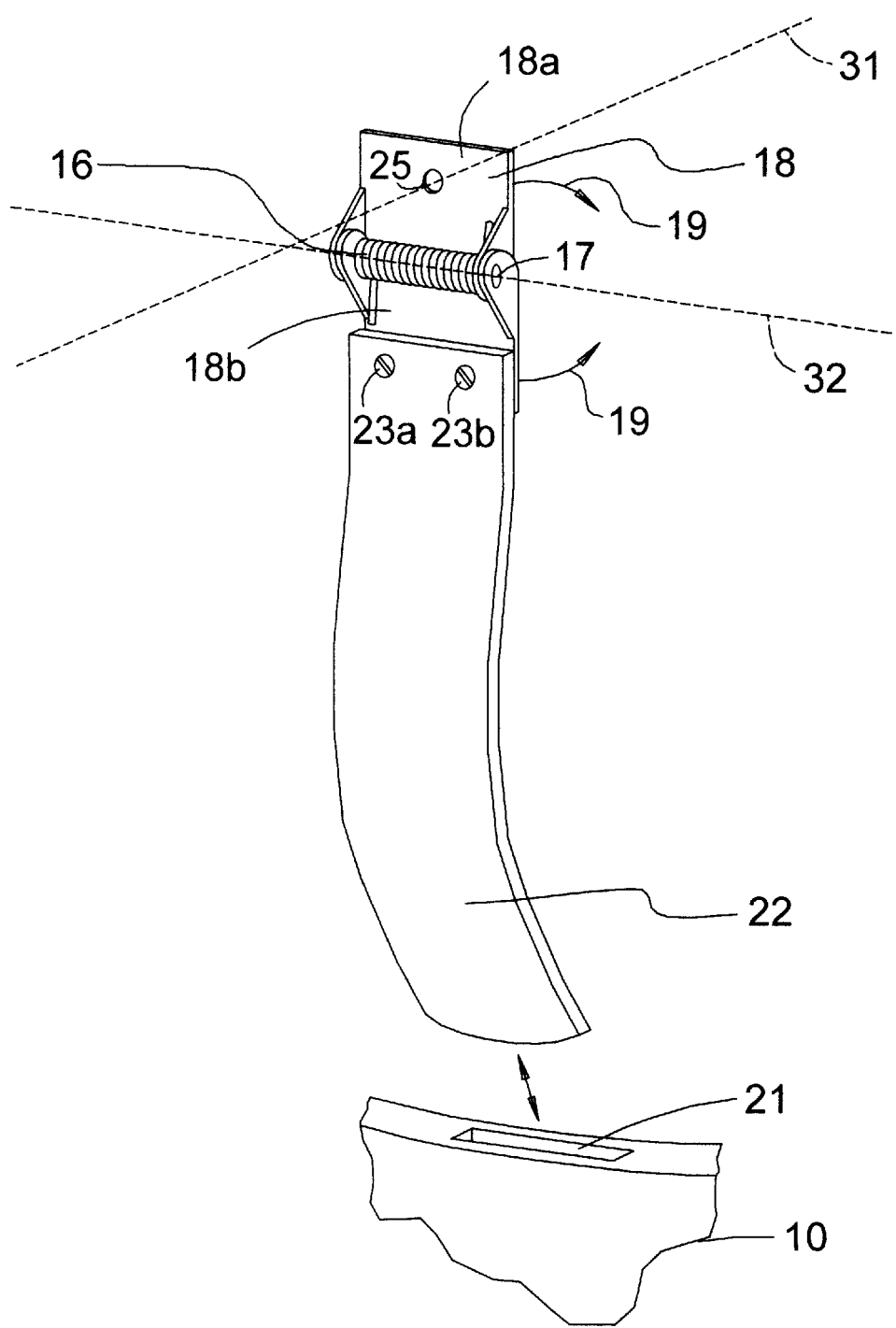
FIG. 4 is a perspective view of a formed extension attached to a spring hinge as employed in the braces of FIGS. 1–3.

FIG. 4 illustrates in more detail, and apart from the remaining portions of brace 8, the springed hinge 18, extension 22 attached thereto, and shoe 10. Hinge 18 includes an upper leaf 18a and a lower leaf 18b with a pin 17 establishing a hinged or rotatable relationship therebetween. Spring 16 surrounds pin 17 and biases upper portion 18a and lower portion 18b to produce closing forces 19 as described above. Spring 16 thereby aids in lifting ones foot when needed to avoid drop foot such as when walking, however, spring 16 does not interfere significantly with use of the foot such as in natural sitting or relaxing postures. Spring 16 can be selected in strength to provide sufficient lifting support to avoid drop foot hazards but not to introduce sufficient forces to interfere with normal use of the foot or postures taken in normal sitting conditions. Thus, the user's ankle need not be restricted to a 90 degree angle and the user enjoys more natural use of the foot in walking, sitting and relaxing.

Extension 22 attaches in fixed relation, i.e., at screws 23a and 23b to lower leaf 18b. As such, extension 22 is in substantially fixed relation relative to springed hinge 18. Lower leg support 12, however, enjoys some degree of movement relative to springed hinge 18. More particularly, upper leaf 18a includes an aperture 25 centrally located on leaf 18a above spring 16. Lower leg support 12 includes a corresponding aperture 27 and a fastener 29 extends through apertures 25 and 27 to maintain leaf 18a and lower leg support 20 in face-to-face contact. Accordingly, closing forces 19 produced by springed hinge 18 are fully transmitted through the face-to-face contact of upper leaf 18a and lower leg support 12. This coupling, however, allows relative rotation between lower leg support 12 and springed hinge 18 about a front-to-rear axis of rotation 31 (FIGS. 1 and 4). Springed hinge 18 establishes a left-to-right axis of rotation 32 (FIGS. 2 and 4). In this manner, brace 18 allows certain unrestricted movement of the person's ankle while still maintaining application of closing forces 19 to aid against drop foot.

FIG. 4 also illustrates the mounting arrangement provided between extension 22 and slot 21 of shoe 10. Extension 22 removably engages shoe 10 by insertion within slot 21. Slot 21, being integral to heel support 20, thereby establishes a substantially fixed relationship between extension 22 and shoe 10. Thus, closing forces 19 produced at springed hinge 18 result in lifting forces 30 from the perspective of the user. The length of extension 22 relative to the depth of slot 21 dictates the position, i.e., height, of springed hinge 18 relative to the user's ankle. As may be appreciated, variation in extension 22 length may be employed to more precisely position axis of rotation 32 relative to a particular user's anatomy. This coupling arrangement provided between the upper portion of brace 8 and the modified shoe 10 makes convenient removal of extension 22 from shoe 10 when desired. For example, the user may wish to remove the upper portion of brace 8 while sitting or relaxing. When needed, however, the user may conveniently re-insert extension 22 in slot 21 and establish aid against drop foot.

Figure 5:
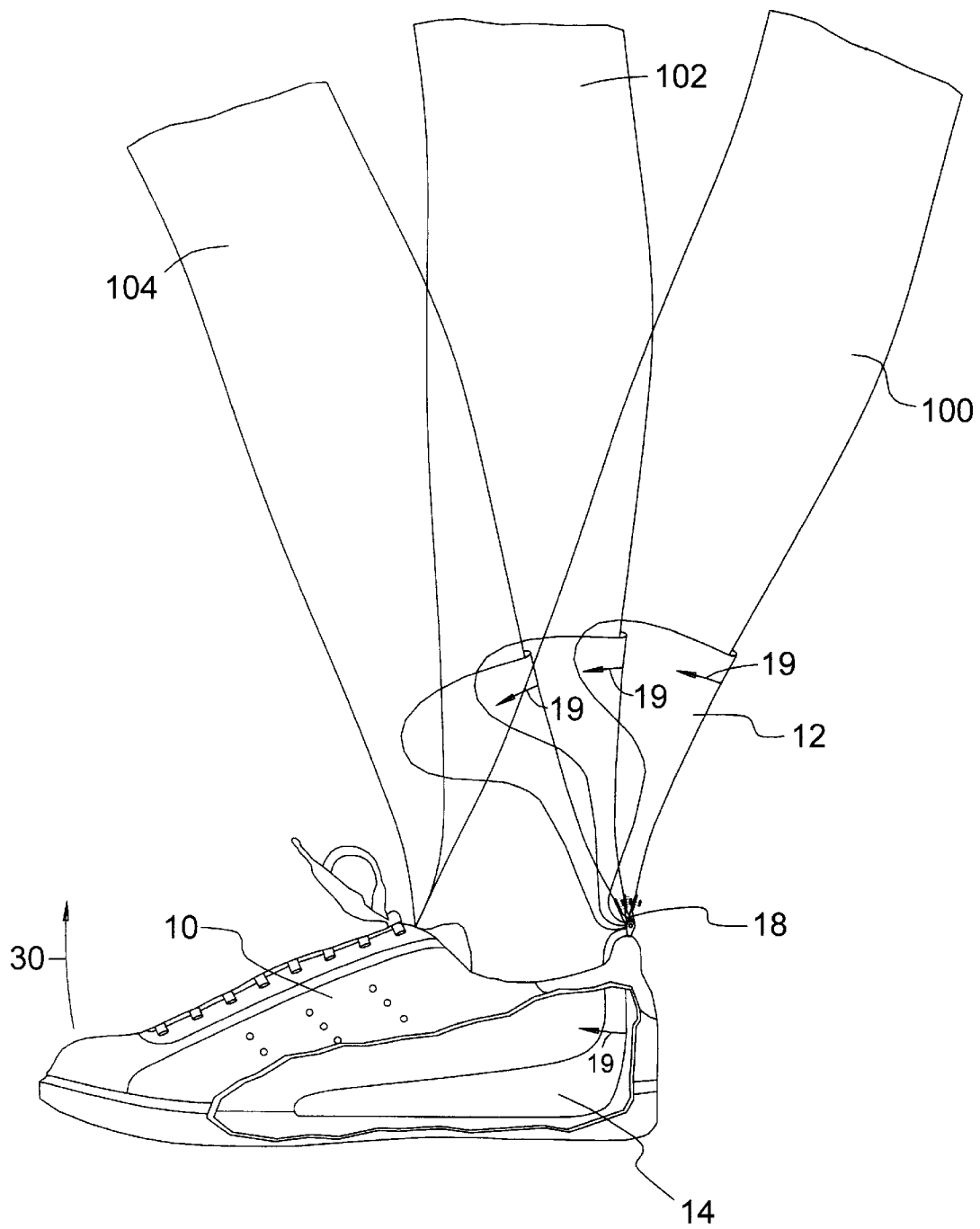
FIG. 5 is a side elevational view showing use of the brace of FIGS. 1–2 when walking, sitting, or relaxing.

FIG. 5 illustrates use of brace 8', and brace 8 as well, as the user bends the ankle such as when walking. In FIG. 5, foot support 14 remains captured within shoe 10 and hinge 18 remains in substantially fixed position relative to the user's ankle. Due to the closing forces 19 established by brace 8', leg support 12 bears in each position against the back of the user's leg. More particularly, in an extended toe position 100, closing forces 19 are maximized and result in a maximum lifting force 30. In this manner, brace 8' aids against drop foot by maximizing lifting force 30 when most-needed. In the normal position 102, i.e., ankle at substantially 90 degrees, lifting forces 19 remain, but at a lesser magnitude thereby interfering less with normal walking movement. In the closed position 104, i.e., toe retraction, lifting forces 19 are minimized and offer little interference with normal walking movement. At all times, leg support 12 remains against the user's leg and maintains the necessary lifting forces 19 to aid against foot drop.

Support 12 moves slightly relative to the user's leg, however, because it need not be fixed to the user's leg to maintain the necessary lifting forces 19. More particularly, support 12 is unrestricted in moving vertically relative to the user's leg as the ankle bends. In this aspect of the present invention, brace 8' offers little discomfort as the ankle moves relative to the leg and brace 8' pivots about axis 32 (FIGS. 2 and 4). Furthermore, due to the freedom of movement about axis 31 (FIGS. 1 and 4) support 12 allows lateral movement of the ankle without interference. Give such multiple degrees of freedom while still aiding against foot drop, brace 8' enhances comfort not only while walking but also while in sitting or other relaxing postures.

Thus, even without removing brace 8', the user enjoys significantly greater comfort relative to other drop foot braces. The user always has the option, however, to easily remove extension 22 and dismount brace 8' when desired for even greater comfort and flexibility when in sitting or other relating postures.

Figure 6:
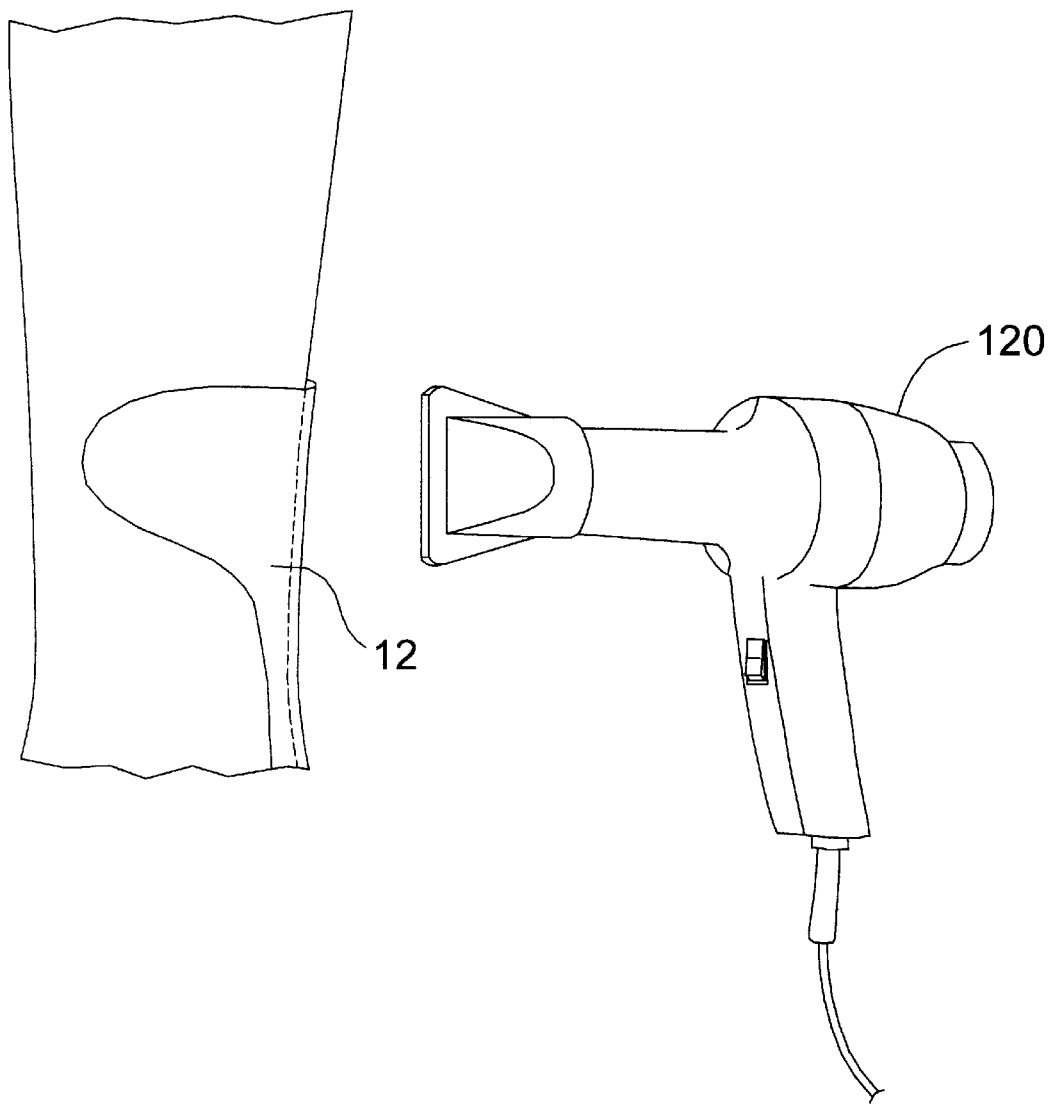
FIG. 6 is a perspective view showing a heat gun as applied to a portion of the brace to custom fit the brace to the user's body contour.

FIG. 6 illustrates use of a heat gun 120 to customize a leg support 12 relative to a user's anatomical contours. Material forming support 12 responds to heat and becomes pliable. In this form, support 12 may be pressed against the user's leg to establish a custom fit thereto for better comfort, concealment, and coupling to the user's leg. Once cooled, support 12 assumes a more rigid form and remains in the customized shape.

Figure 7:
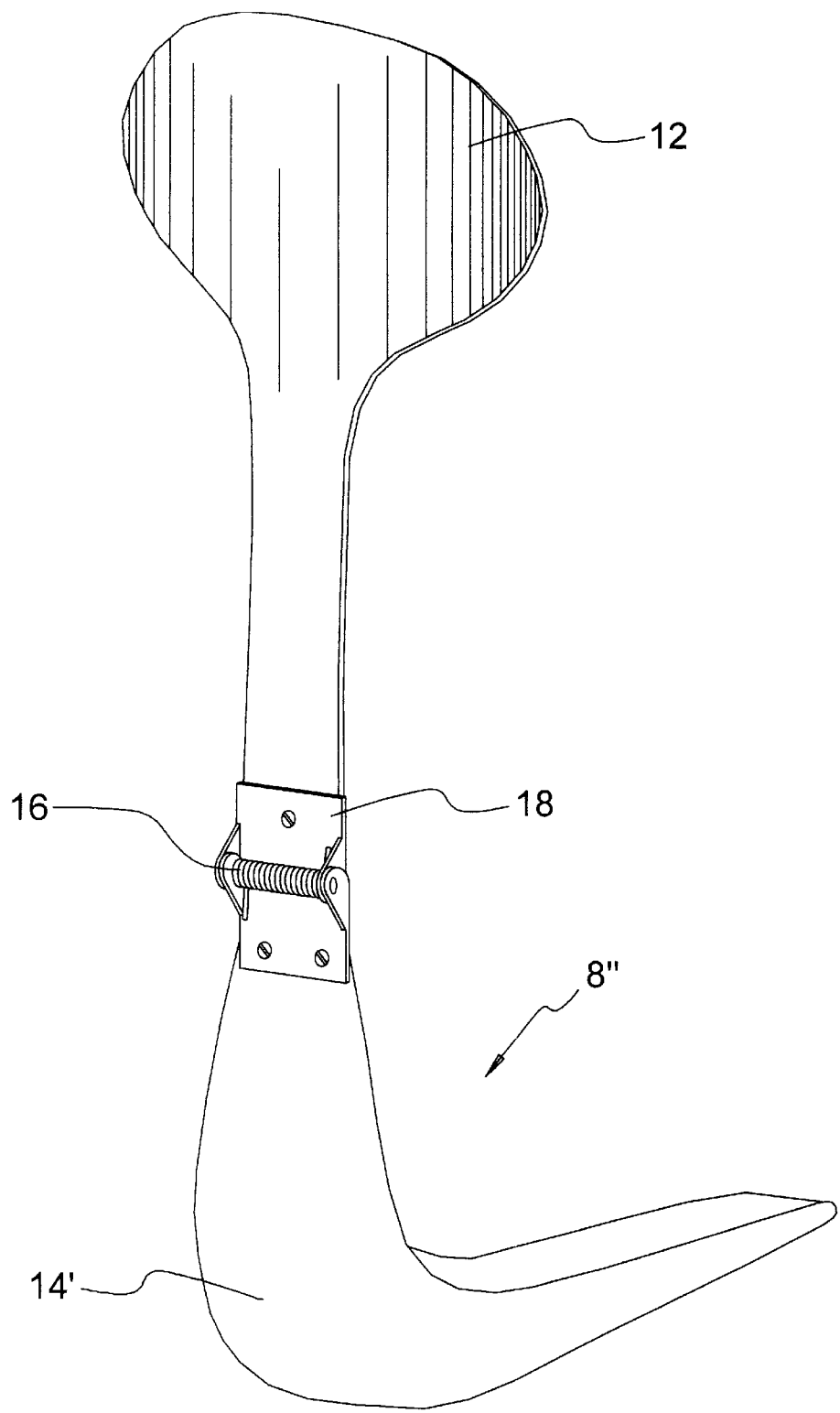
FIG. 7 is a rear perspective view of a third form of the present invention provided as a stand-alone brace useable in conjunction with a conventional shoe.

FIG. 7 illustrates a third form of the present invention, a stand-alone brace 8" including a leg support 12 and a springed hinge 18 as discussed above. Brace 8" includes an independent foot support 14', i.e., not integrated into a show structure. This allows use of brace 8" with a variety of conventional shoes by inserting support 14' into the shoe during use. Brace 8" otherwise operates in substantially the same manner as braces 8 and 8' as discussed above. To remove brace 8", one need only remove one's shoe. Brace 8" offers all the advantages of aid against foot drop while not interfering significantly with normal walking, sitting or relaxing positions.

Figure 8:
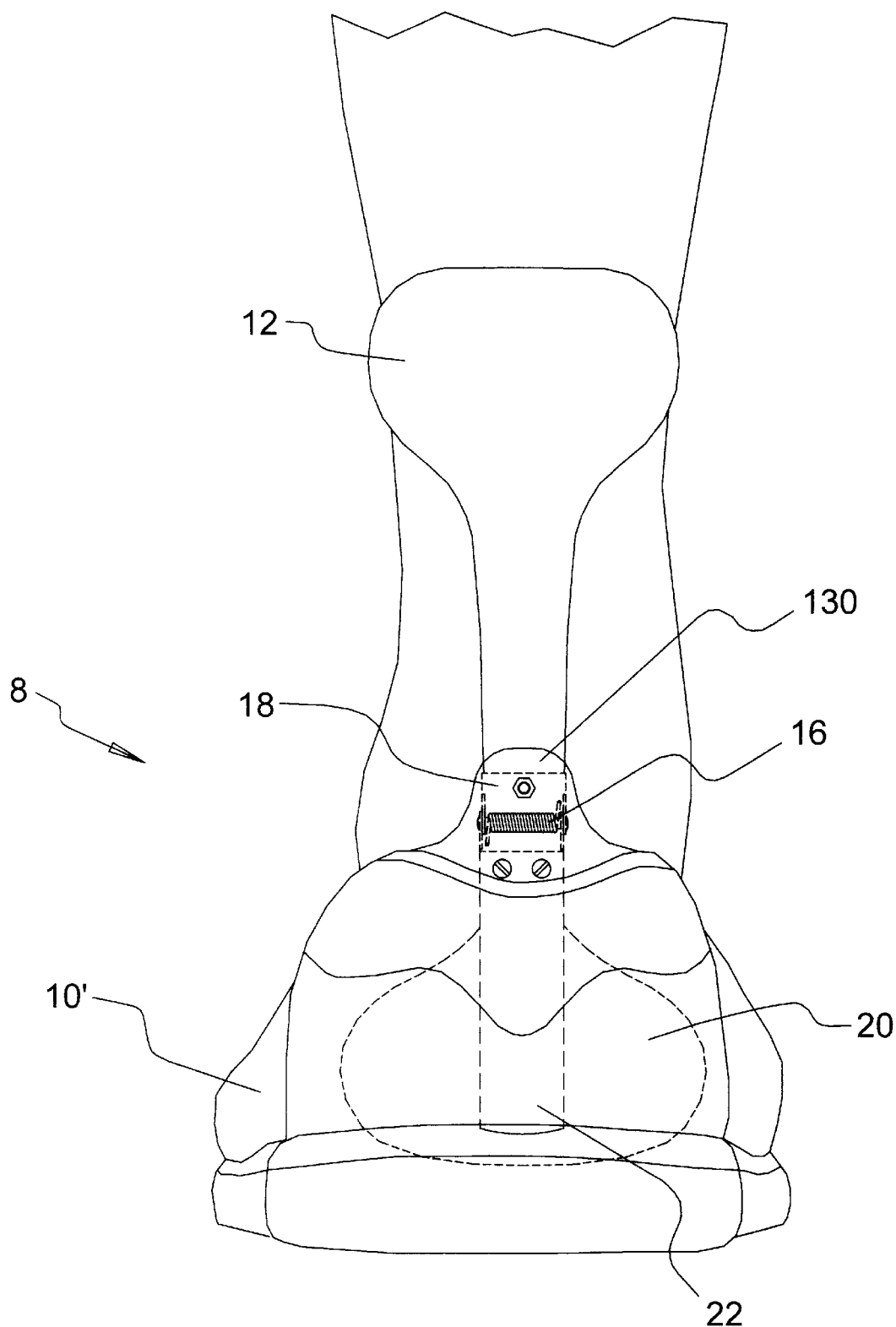
FIG. 8 is a rear view of a brace according to the present invention similar to that of FIG. 2, but showing a tab portion of the shoe concealing the springed hinge of the brace.

FIG. 8 illustrates use of a tab structure 130 on a modified shoe 10'. The brace illustrated in FIG. 8 can be any one of braces 8, 8', or 8". Tab 130 extends upward at the heel of shoe 10 and conceals hinge 18 without interfering with use or operation brace 8. While a brace under the present invention is substantially concealed even with a tab structure 130, use of a tab structure 130 enhances concealment and encourages the user to make use of the brace 8.

Thus, an improved drop foot brace has been shown and illustrated. During walking, gravity causes the toe of the foot to drop. The springed hinge 18 provides an opposing force keeping the toe of the foot in an elevated position and avoiding dragging or stumbling. The force generated by the springed hinge 18 keeps the foot in an elevated position, but lets the wearer move his foot if desired such as during sitting or relaxing. The heel or foot support, formed extension and the formed lower leg support provide a framework for distributing the spring hinge closing forces. The lower leg support, spring hinge and formed extension slide with the movement of the ankle along the back of the lower leg in a vertical motion when the person extends the toe of the foot such as when relaxing or sitting. Further, a single attachment aperture in the upper leaf of the spring hinge allows rotation of the spring hinge normal to the movement of the spring hinge axis of rotation. This maintains a mechanical connection between the lower leg support and the spring hinge to support the foot against drop foot, but allows lateral flexibility for comfort.

The device is substantially concealed under clothing when in use. The subject matter of the present invention thereby address the important aspect of concealment. Persons making use of prosthetic devices prefer, if possible, to conceal the devices and find great utility in such concealment. Integrating heel support 20 or formed foot support 14 into a modified shoe 10 aids in establishing better concealment of brace 8, e.g., such as by extending a tab structure 130 up above the heel to, for example, cover portions of brace 8, i.e., cover hinge 16.

With respect to the positioning of hinge 16, positioning hinge 16 directly above the rear upper rim of the shoe generally suitably positions hinge 16 with respect to the bend of the user's ankle. However, if desired one can provide extensions 22 of varying length whereby a user may select one of such extensions 22 for attachment to hinge 18 and thereby adjust the vertical position of hinge 18 to fine tune the relationship between the pin 17 and bend of the user's ankle.

The brace of the present invention has an advantage in that it doesn't restrict the sideways movement of the foot, in other words, the arcing movement of the toes about the axis of the leg and allows the sideways dragging of the foot or otherwise moving the foot forward in contrast to many braces which have a rigid structure especially those which have structures coming down the outside edges of the outside of the ankle on both sides severely restrict the foot to strictly ankle hinge type movement and don't allow any sidewise pivoting movement. As a result, the brace under the present invention allows the ankle and foot to interact in as natural a relationship as possible while still providing support when necessary to lift the foot without interfering significantly with other use of the foot or comfort in sitting postures or non-walking conditions.

There are a range of possible springs that can be used that provide the desired function of providing aid in lifting the foot but not interfering with use of the foot in walking or sitting postures. This will depend on the degree of assistance required by the individual, i.e., the severity of the drop foot condition, as well as weight concerns regarding the weight of the shoe and the person's foot. In other words, the spring could be ultra fine-tuned for a particular individual's needs per medical condition as well as the size of the foot and the weight of the shoe.

It will be appreciated that the present invention is not restricted to the particular embodiment that has been described and illustrated, and that variations may be made therein without departing from the scope of the invention as found in the appended claims and equivalents thereof.

What is claimed is:

1. A prosthetic device comprising:
   a first support adapted for bearing pressure against the rear of the lower leg of a user;
   a second support adapted for bearing pressure against the rear of the user's heel; and
   a springed hinge coupling said first and second supports and biased to urge said first and second supports toward the user's leg and heel, respectively, whereby upon securing said hinge against the user's leg in the vicinity of the user's ankle said user experiences a foot lifting force.

2. A device according to claim 1 wherein said brace further comprises a shoe adapted for maintaining said hinge against the rear portion of the user's leg in the vicinity of the user's ankle.

3. A prosthetic device comprising:
   a shoe including at its heel a brace receiving formation;
   an upper support adapted for bearing pressure against the rear lower portion of a user's leg;
   an extension adapted for mounting within said brace mounting formation of said shoe; and
   a springed hinge coupling said support and said extension whereby upon placement of said extension in said brace mounting formation said springed hinge biases said support toward said rear of the user's lower leg and biases said extension forward toward the user's heel when said user's foot is placed within said shoe whereby said springed hinge is maintained substantially behind the user's ankle and the user experiences a foot lifting force.

4. A device according to claim 3 wherein said shoe further comprises a heel support integrally formed therewith and including said brace receiving formation.

5. A device according to claim 3 wherein said brace receiving formation is a slot formation and said extension of corresponding complimentary shape.

6. A device according to claim 3 wherein said shoe further comprises a cupped foot support substantially surrounding the rear and side portions of said heel and extending out underneath the user's foot and integral to said brace receiving formation.

7. A device according to claim 3 wherein said brace allows freedom of movement of the user's foot in toe extension and retraction directions.

8. A device according to claim 3 wherein said device allows freedom of movement of the user's foot in side-to-side directions.

9. A drop foot brace device for a user having a leg, a foot and an ankle, the ankle coupling the leg and foot, said brace device comprising:
   a leg support adapted to bear pressure against a rear portion of the user's leg above the ankle;
   a foot support adapted to bear pressure against a rear portion of the user's foot below the ankle;
   a springed hinged coupling said leg support and said foot support, said hinge allowing rotation about a first axis of rotation generally parallel to rotation of the ankle corresponding to toe extension and retraction; and
   a shoe structure surrounding said user's foot and maintaining said springed hinged at a selected location relative to the user's ankle whereby said springed hinge urges said leg support toward the rear portion of the user's leg and urges said foot support toward said rear portion of the user's foot to urge said foot toward toe retraction.

10. A device according to claim 9 wherein said springed hinge allows rotation about a second axis of rotation generally transverse to said first axis of rotation.

11. A device according to claim 9 wherein said springed hinge comprises:
    an upper leaf coupled to said leg support;
    a lower leaf rotatably coupled at an upper portion thereof to said upper leaf, said lower leaf coupled at a lower portion thereof to said foot support; and
    a spring biasing said leg support against the rear portion of the leg and against the rear portion of the foot.

12. A device according to claim 11 wherein said upper leaf and said leg support couple to allow rotation of said leg support relative to said upper leaf about a second axis of rotation generally transverse to said first axis of rotation.

13. A device according to claim 9 wherein foot support comprises a cupped heel support.

14. A device according to claim 13 wherein said cupped heel support is integral to said shoe.

15. A device according to claim 13 wherein said cupped heel support is insertable into said shoe.

16. A device according to claim 9 wherein foot support comprises a structure extending across a bottom of the user's foot.

17. A device according to claim 16 wherein said foot support is integral to said shoe.

18. A device according to claim 16 wherein said foot support is insertable into said shoe.

19. A device according to claim 9 wherein shoe includes a slot and said foot support comprises an extension adapted to engage said slot.

* * * * *